US00PP30372P3

(12) United States Plant Patent
Skotak, Jr.

(10) Patent No.: US PP30,372 P3
(45) Date of Patent: Apr. 9, 2019

(54) ***GUZMANIA* PLANT NAMED 'DURAPRI'**

(50) Latin Name: *Guzmania lingulata*
Varietal Denomination: DURAPRI

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 15/732,214

(22) Filed: Oct. 4, 2017

(65) Prior Publication Data

US 2019/0029158 P1 Jan. 24, 2019

(30) Foreign Application Priority Data

Jul. 18, 2017 (QZ) ..... PBR 2017/1807

(51) Int. Cl.
*A01H 5/02* (2018.01)
*A01H 6/22* (2018.01)

(52) U.S. Cl.
USPC ..... Plt./371
CPC ..... *A01H 6/225* (2018.05)

(58) Field of Classification Search
USPC ..... Plt./371
See application file for complete search history.

*Primary Examiner* — Keith O. Robinson
(74) *Attorney, Agent, or Firm* — Samuel R. McCoy, Jr.

(57) ABSTRACT

A new and distinct variety of *Guzmania* plant named 'DURAPRI' which is characterized by the combination of a flattened globular plant profile with foliage arranged in an attractive rosette, relatively short foliage with a dark green upper surface and a greyed-purple lower surface, an inflorescence with a rounded profile, born on a short peduncle, an inflorescence with red floral bracts which are tipped white, and the stability of all characteristics from generation to generation.

4 Drawing Sheets

Latin name of the genus and species: The Latin name of the genus and species of the novel variety disclosed herein is *Guzmania lingulata.*

Variety denomination: The inventive variety of *Guzmania* disclosed herein has been given the variety denomination 'DURAPRI'.

CROSS REFERENCE TO RELATED APPLICATIONS

This application claims priority to the Community Plant Variety Rights application number 2017/1807, filed Jul. 18, 2017, which is herein incorporated by reference.

BACKGROUND OF THE INVENTION

Parentage: The *Guzmania* variety 'DURAPRI' is a seedling selection which resulted from a controlled pollination breeding program. In July of 2007, the inventor performed the controlled cross-pollination of *Guzmania lingulata* 'Fortuna' (not patented), the seed parent, and an unnamed dwarfed seedling progeny of *Guzmania lingulata* 'El Cope' (not patented), the pollen parent, at a commercial greenhouse in Alajuela, Costa Rica. Those skilled in the art recognize that *Guzmania* seed can be difficult to germinate. Therefore, in November of 2007, the seed that resulted from the cross of July 2007 in Alajuela, Costa Rica were shipped by the inventor to a tissue culture laboratory in Evergem, Belgium for in vitro seed germination in order to increase the germination rate. At the direction of the inventor, the resulting seedlings were grown for 6 months to evaluate plant vigor and then shipped back to Alajuela, Costa Rica for further evaluation by the inventor. In November of 2008, the inventor selected one seedling for commercial production due to its unique growth habit and flower characteristics. This new and distinctive cultivar was given the name 'DURAPRI'.

Asexual Reproduction: 'DURAPRI' was first asexually propagated by meristematic tissue culture in January of 2014 at a commercial laboratory in Evergem, Belgium and has since been asexually propagated through 3 additional generations. Through subsequent generations, the unique features of this cultivar are stable and reproduced true to type.

SUMMARY OF THE INVENTION

The cultivar 'DURAPRI' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'DURAPRI'. These characteristics, in combination, distinguish 'DURAPRI' as a new and distinct *Guzmania* cultivar:

1. *Guzmania* 'DURAPRI' exhibits a flattened globular plant profile with foliage arranged in an attractive rosette; and
2. *Guzmania* 'DURAPRI' exhibits relatively short foliage with a dark green upper surface and a greyed-purple lower surface; and
3. *Guzmania* 'DURAPRI' exhibits an inflorescence with a rounded profile, born on a short peduncle; and
4. *Guzmania* 'DURAPRI' exhibits an inflorescence with red floral bracts which are tipped white.

BOTANICAL DESCRIPTION OF THE PLANT

Figure 1:
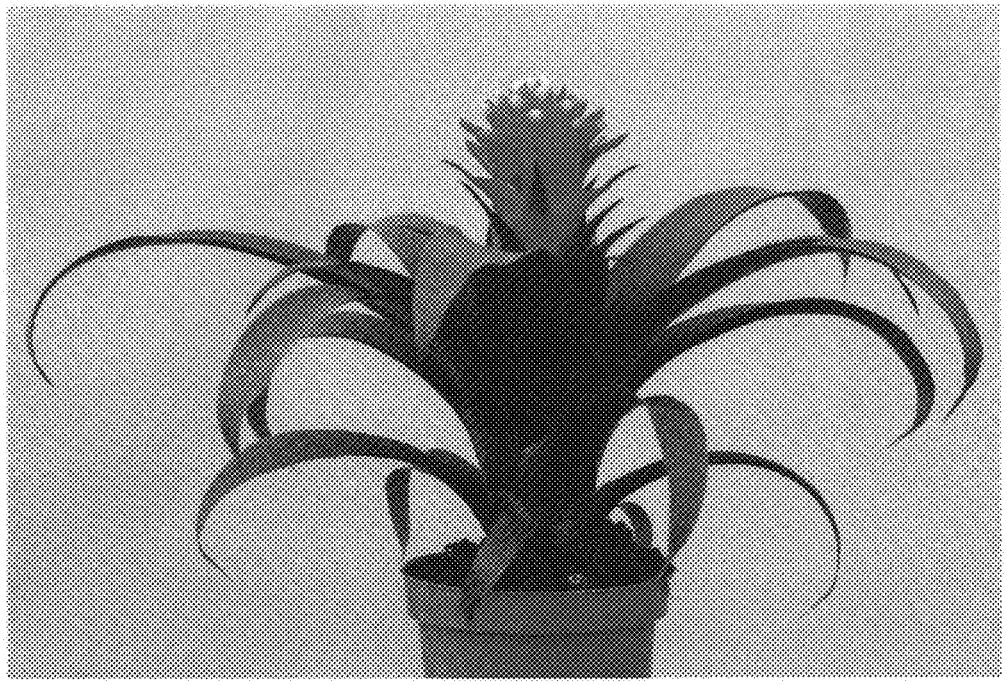
FIG. 1 illustrates, as nearly true as it is reasonably possible to make the same in color photographs of this type, an exemplary plant of 'DURAPRI' grown in a commercial greenhouse in Evergem, Belgium. This plant is approximately 18 month old, shown planted in a 9 cm container.
Figure 2:
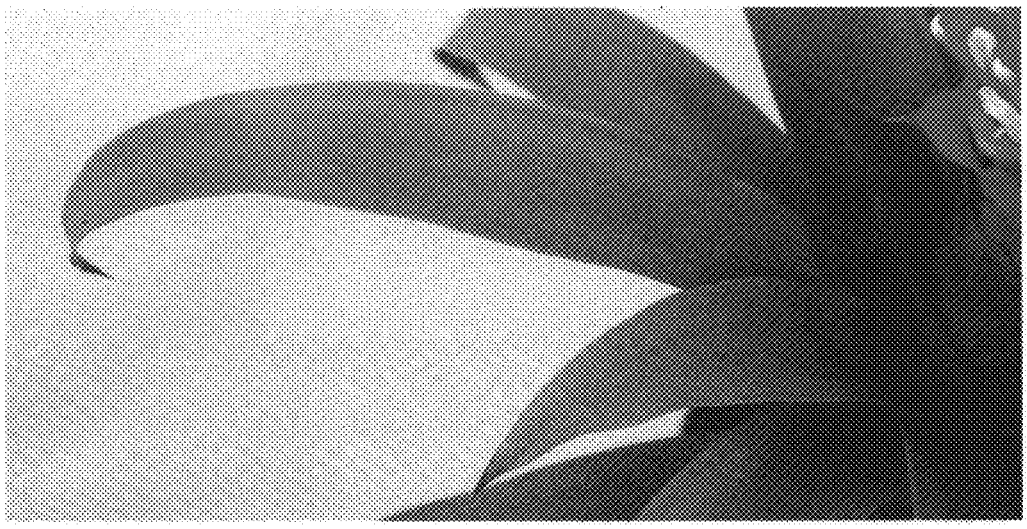
FIG. 2 illustrates, as nearly true as it is reasonably possible to make the same in color photographs of this type, the typical adaxial surface of the mature foliage of 'DURAPRI'.
Figure 3:
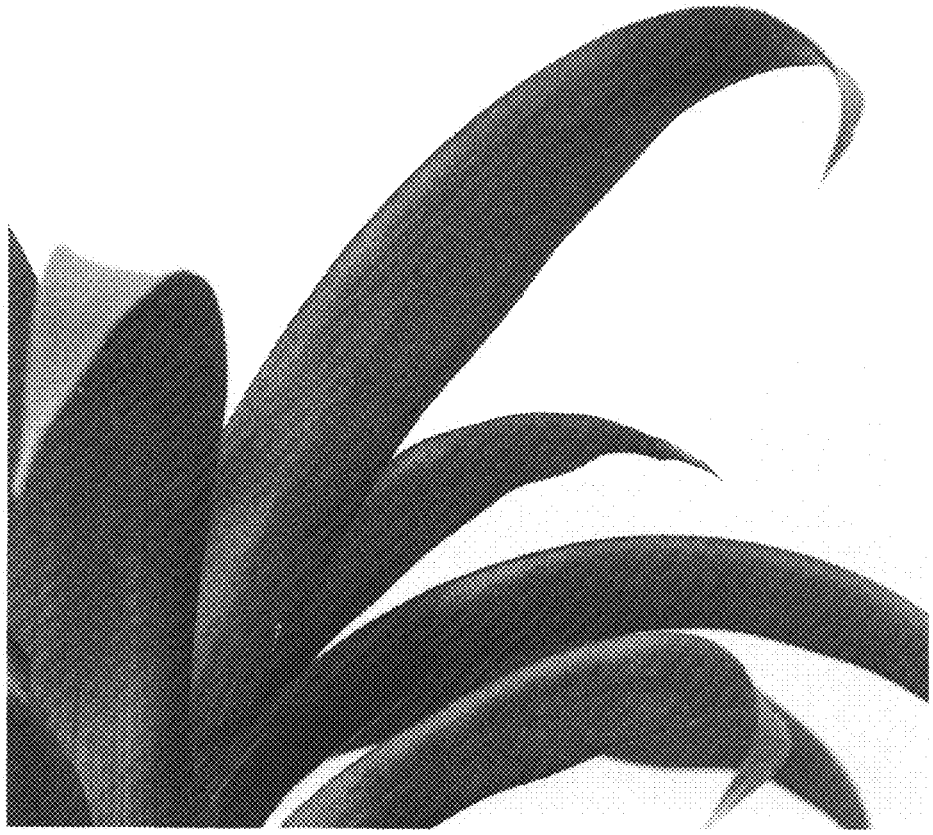
FIG. 3 illustrates, as nearly true as it is reasonably possible to make the same in color photographs of this type, the typical abaxial surface of the mature foliage of 'DURAPRI'.
Figure 4:
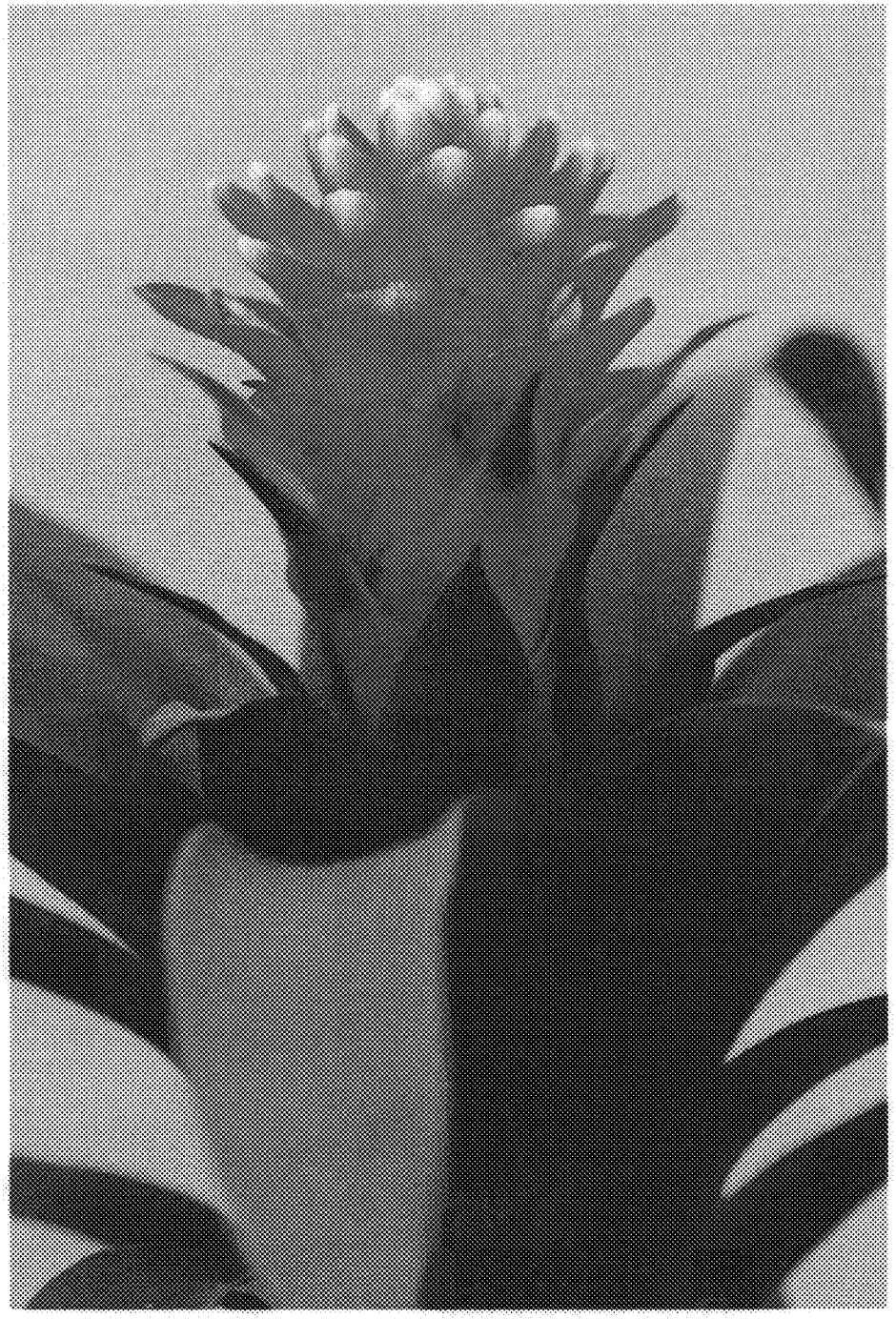
FIG. 4 illustrates, as nearly true as it is reasonably possible to make the same in color photographs of this type, the typical inflorescence of 'DURAPRI'.

The following observations and measurements made in June of 2017 describe averages from a sample set of six specimens of 12 month-old 'DURAPRI' plants grown in 8 cm nursery pots at a commercial greenhouse in Evergem, Belgium. Plants were grown under light maximum light levels of approximately 12,000 lux. Plants were maintained with a fertigation program and regularly watered with overhead irrigation. No chemical pest measures were taken.

Those skilled in the art will appreciate that certain characteristics will vary with older or, conversely, with younger plants. 'DURAPRI' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'DURAPRI' and a comparison with the parent plants and most similar variety of *Guzmania* are provided below.

Plant description:

*Growth habit.*—Perennial; monopodial; broad, upright. Leaves arranged in a basal rosette, with no lateral branching, and the inflorescence growing from the center of the basal rosette.

*Plant form.*—Flattened globular.

*Average height.*—13.0 cm, from the soil level to the top of the foliar plane, and 16.5 to the top of the floral plane.

*Plant spread.*—Average of 31.0 cm.

*Growth rate.*—Low.

*Plant vigor.*—Low to moderate.

*Propagation type.*—Mericloning.

*Time to initiate roots.*—Approximately 14 days to initiate roots at 22 degrees Celsius.

*Time to produce a finished plant.*—Approximately 12 months are needed to produce a marketable plant in an 8 cm container.

*Pest resistance and susceptibility.*—Neither resistance nor susceptibility to typical *Guzmania* pests and diseases has been observed.

*Temperature tolerances.*—USDA Zones 10 to 12; at least tolerant of temperatures to 40 degrees Celsius. High tolerance to rain inundation; high tolerance to wind.

Root system:

*General.*—Thick; medium density.

*Texture.*—Slightly fleshy.

Foliage:

*Arrangement.*—Rosulate. No stems or lateral branches, the leaves form a stem-like structure not consisting of a stem as such, but only consisting of the leaf sheaths.

*Attachment.*—Sheathed.

*Division.*—Simple.

*Quantity of leaves.*—16.

*Lamina.*—Dimensions — 23.8 cm long and 3.0 cm wide. Thickness — Approximately 0.9 cm. Shape of blade — Ensiform. Aspect — Slightly concave. Attitude — Moderately reflexed. Apex — Apiculate. Base — Sheathing. Margin — Entire; not undulated. Pubescence, texture and luster of adaxial surface — Glabrous, smooth and matte. Pubescence, texture and luster of abaxial surface — Glabrous, smooth and slightly glossy. Color — Juvenile foliage, adaxial surface — Yellow-green, nearest to in between RHS 147A and 147B; middle section is greyed-purple, nearest to RHS N186C; fading lighter towards the base, nearest to RHS 184A. Juvenile foliage, abaxial surface — Greyed-purple, nearest to RHS N186C; fading lighter towards the base, nearest to RHS 184A. Mature foliage, adaxial surface — Green, nearest to RHS NN137B; fading to yellow-green towards the base, nearest to in between RHS 152A and 152B. Mature foliage, abaxial surface — Greyed-purple, nearest to RHS N186C. Venation — Pattern — Parallel. Mature foliage venation, adaxial surface — Green, nearest to RHS NN137B; veins at the base are greyed-purple, nearest to RHS 184A. Mature foliage venation, abaxial surface — Greyed-purple, nearest to RHS N186C, and darker towards the base, nearest to RHS 184A.

*Sheath.*—Sheath length — Average 6.4 cm. Sheath width — Average 6.3 cm. Sheath color — In between greyed-yellow and greyed-brown, nearest to RHS 161A and 199D, respectively; veined greyed-purple, nearest to a combination of RHS 183A and 183B.

Inflorescence:

*Inflorescence arrangement.*—Terminal spike with showy bracts and an average of 26 flowers.

*Inflorescence position.*—Above the foliage.

*Natural flowering season.*—Continuously.

*Time to flower.*—Approximately 6 months.

*Inflorescence quantity.*—One.

*Flowers per inflorescence.*—Average of 26, with 10 open flower and 16 in bud stage and not opening.

*Inflorescence height.*—Approximately 6.1 cm (measured from base of lowest flower to top of upper flower).

*Inflorescence diameter.*—Average of 4.2 cm, excluding bracts, and 6.0 cm with bracts.

*Peduncle.*—Dimensions — Approximately 10.2 cm long and 0.8 cm in diameter. Aspect — Vertical. Strength — Strong. Texture and luster — Glabrous, smooth, and very slightly glossy. Color — White, RHS NN155B.

Bud:

*Length.*—Average of 1.7 cm.

*Diameter.*—Average of 0.4 cm.

*Shape.*—Lanceolate.

*Texture and luster.*—Glabrous, smooth, and moderately glossy.

*Color.*—White, nearest to RHS NN155B.

Flower:

*Flower type and form.*—Single; oblanceolate to narrow oblong.

*Attachment.*—Sessile.

*Aspect.*—Upright.

*Flowering habit.*—Freely flowering; continuous.

*Height.*—Approximately 0.6 cm.

*Diameter.*—Average of 0.6 cm.

*Depth.*—Approximately 3.1 cm.

*Floral throat diameter.*—0.2 cm.

*Floral throat texture.*—Glabrous; smooth.

*Diameter of floral tube.*—0.2 cm.

*Length of floral tube.*—2.2 cm.

*Floral tube texture, outer and inner surfaces.*—Glabrous; smooth.

*Fragrance.*—No fragrance.

*Lastingness.*—4 weeks.

*Persistent.*—Persistent.

*Petals.*—Quantity of Petals — 3. Arrangement — Rotate; single whorl of fused petals with the proximal 75% of the petals fused. Length — Approximately 2.8 cm. Width — Approximately 0.4 cm. Shape — Narrow spatulate; concave. Apex — Obtuse. Base — Fused into a tube. Margin — Entire; not undulated. Pubescence, texture and luster of upper surface — Glabrous, smooth and matte. Pubescence, texture and luster of lower surface — Glabrous, smooth and very slightly glossy. Color when opening, upper surface — White, nearest to in between RHS 155A and 155B. Color when opening, lower surface — White, nearest to in between RHS 155A and 155B. Color when fully opened, upper surface — White, nearest to in between RHS 155A and 155B. Color when fully opened, lower surface — White, nearest to in between RHS 155A and 155B. Fading, upper surface — Not fading. Fading, lower surface — Not fading. Venation color, fully opened, upper surface — No venation is visible. Venation color, fully opened, lower surface — No venation is visible. Floral throat color — White, nearest to in between RHS 155A and 155B. Floral throat venation color — No venation is visible. Floral tube color, when fully opened — Yellow-white, nearest to RHS 158D. Floral tube venation color — No venation is visible.

*Calyx.*—Shape — Rotate. Length — Average of 1.7 cm. Diameter — Average of 0.6 cm.

*Sepals.*—Quantity — 3 unfused sepals in a single whorl. Arrangement — Rotate. Length — 1.7 cm. Width — 0.4 cm. Shape — Lanceolate. Apex — Acute. Base — Cuneate. Margin — Entire. Pubescence, texture and luster of upper surface — Glabrous, smooth, and matte. Pubescence, texture and luster of lower surface — Glabrous, smooth, and slightly glossy. Color when opening, upper surface — White, nearest to in between RHS 155A and 155B. Color when opening, lower surface — White, nearest to in between RHS 155A and 155B. Color when fully opened, upper surface — White, nearest to in between RHS 155A and 155B. Color when fully opened, lower surface — White, nearest to in between RHS 155A and 155B.

*Bract.*—General — One large, colorful bract at the base of each individual flower. Quantity — Average of 15. Shape — Broad ovate to broad oblong; concave. Dimensions — Average of 4.2 cm long, including the sheath, and 1.9 cm wide. Apex — Obtuse. Base — Broad cuneate. Margins — Entire. Texture and luster, upper surface — Smooth and moderately glossy. Texture and luster, lower surface — Smooth and moderately glossy. Uppermost immature bract color, upper surface — Red, nearest to RHS 44A, and fading lighter towards the base, nearest to RHS 44C; apex is white, nearest to RHS NN155D. Uppermost immature bract color, lower surface — Red, nearest to RHS 44B, and fading lighter towards the base, nearest to RHS 44D; apex is white, nearest to RHS NN155D. Mature bract color, upper surface — Red, nearest to RHS 44A, and fading lighter towards the base, nearest to RHS 44C. Mature bract color, lower surface — Red, nearest to RHS 44A; apex is greyed-purple, nearest to RHS N186C. Venation — No venation is visible.

Reproductive organs:

*Stamens.*—Quantity — 6, on average. Anthers — Shape — Dorsifixed; linear. Dimensions — Average of 0.4 cm long and 0.075 cm wide. Color — Greyed-brown, nearest to RHS N199A. Filaments — Length — 0.2 cm, on average. Color — White, nearest to RHS 155A. Pollen — Abundance — Moderately abundant. Color — Yellow-white, nearest to in between RHS 158B and 158C.

*Pistil.*—Quantity — 1. Length — 0.6 cm. Style — Length — 0.5 cm. Color — Greyed-brown, nearest to RHS N199B. Stigma — Shape — Club-shaped. Dimensions — Average of 0.1 cm long and 0.1 cm wide. Color — Greyed-brown, nearest to RHS N199B. Ovary color — Brown, nearest to in between RHS 200C and 200D.

Fruit and seed: To date, not observed.

COMPARISONS WITH THE PARENT PLANT

Plants of the new cultivar 'DURAPRI' differ from its seed parent, *Guzmania lingulata* 'Fortuna' (not patented), by the characteristics described in Chart 1.

CHART 1

| Characteristic | 'DURAPRI' | 'Fortuna' |
|---|---|---|
| Length of foliage. | Short. | Long. |
| Peduncle length. | Shorter than 'Fortuna'. | Longer than 'DURAPRI' |
| General profile of the inflorescence. | Rounded. | Flat. |

Plants of the new cultivar 'DURAPRI' differ from its pollen parent, an unnamed miniature form of *Guzmania lingulata* 'El Cope' (not patented), by the characteristics described in Chart 2.

CHART 2

| Characteristic | 'DURAPRI' | The pollen parent. |
|---|---|---|
| Inflorescence attitude. | Erect. | Not as upright as 'DURAPRI'. |
| Length of foliage. | Short. | Long. |
| Inflorescence height. | Short; compact. | Tall; elongated. |

COMPARISON WITH THE MOST SIMILAR *GUZMANIA* CULTIVAR KNOWN TO THE INVENTOR

'DURAPRI' is similar in many horticultural characteristics to the commercial cultivar *Guzmania* 'DURAREV' (U.S. Plant Pat. No. 24,996). However 'DURAPRI' differs from 'DURAREV' by the characteristics described in Chart 3.

CHART 3

| Characteristic | 'DURAPRI' | 'DURAREV' |
|---|---|---|
| General profile of the inflorescence. | Rounded. | Flat. |
| General coloration of the floral bract tip. | White. | Red. |

That which is claimed is:

1. A new and distinct variety of *Guzmania* plant named 'DURAPRI', substantially as described and illustrated herein.

* * * * *